United States Patent [19]

Swicegood et al.

[11] Patent Number: 5,244,455
[45] Date of Patent: Sep. 14, 1993

[54] KNEE HINGE

[75] Inventors: George D. Swicegood, Hiddenite; Henry L. Richbourg, Jr., Charlotte, both of N.C.

[73] Assignee: Clinitex Corporation, Huntersville, N.C.

[21] Appl. No.: 732,621

[22] Filed: Jul. 19, 1991

[51] Int. Cl.$^5$ .............................. A61F 5/00
[52] U.S. Cl. ........................ 602/16; 602/26
[58] Field of Search ............ 602/5, 16, 20, 23, 26, 602/27; 623/27, 39

[56] References Cited

U.S. PATENT DOCUMENTS

| 4,379,463 | 4/1983 | Meier et al. ............ 602/26 X |
| 4,655,201 | 4/1987 | Pirmantgen ............. 602/16 |
| 4,738,252 | 4/1988 | Friddle et al. ............ 602/16 |
| 4,773,404 | 9/1988 | Townsend ............... 602/26 X |
| 4,890,607 | 1/1990 | Townsend . |
| 5,009,223 | 4/1991 | DeFonce ............... 602/26 X |
| 5,105,805 | 4/1992 | LaPointe et al. ......... 602/26 X |

Primary Examiner—Richard J. Apley
Assistant Examiner—Linda C. M. Dvorak
Attorney, Agent, or Firm—Ralph H. Dougherty

[57] ABSTRACT

A knee brace includes a novel knee hinge having a first arm member, a second arm member, and a cover piece. The first arm member serves as a femoral brace. A cam follower is mounted on one side of the first arm member. The second arm member serves as a tibial brace. The second arm member includes a generally heart-shaped aperture which is a cam for the hinge. The cam defines a continuous cam wall which is adapted to receive and mate with the cam follower. The dimensions of the cam are such that upon engagement of the cam follower with the cam, each semicircular end of the cam follower is in slidable contact with the cam wall during movement of the cam follower, and the edge of the cam follower closest to the cam node is in slidable contact with the cam node during movement of the cam follower. The cam follower rotates about the cam node and permits a degree of motion between full flexion and full extension. The cover piece is adapted for placement atop the mated first and second arm members. The cover piece, second arm member, and first arm member are secured by rivets. The cam follower is therefore bounded on its top by the cover piece, on its bottom by the first arm member, and on its sides by the cam wall of the second arm member.

24 Claims, 2 Drawing Sheets

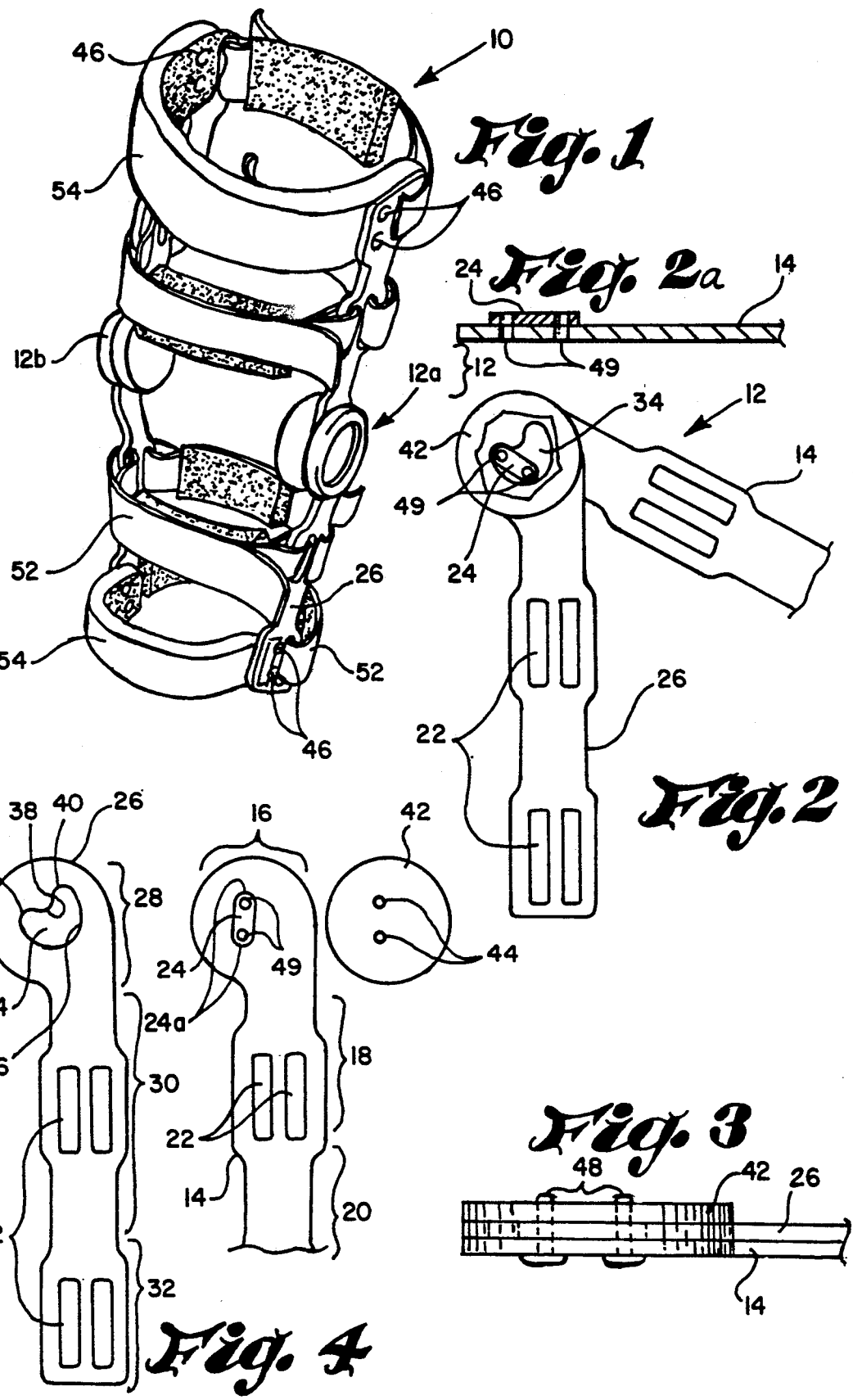

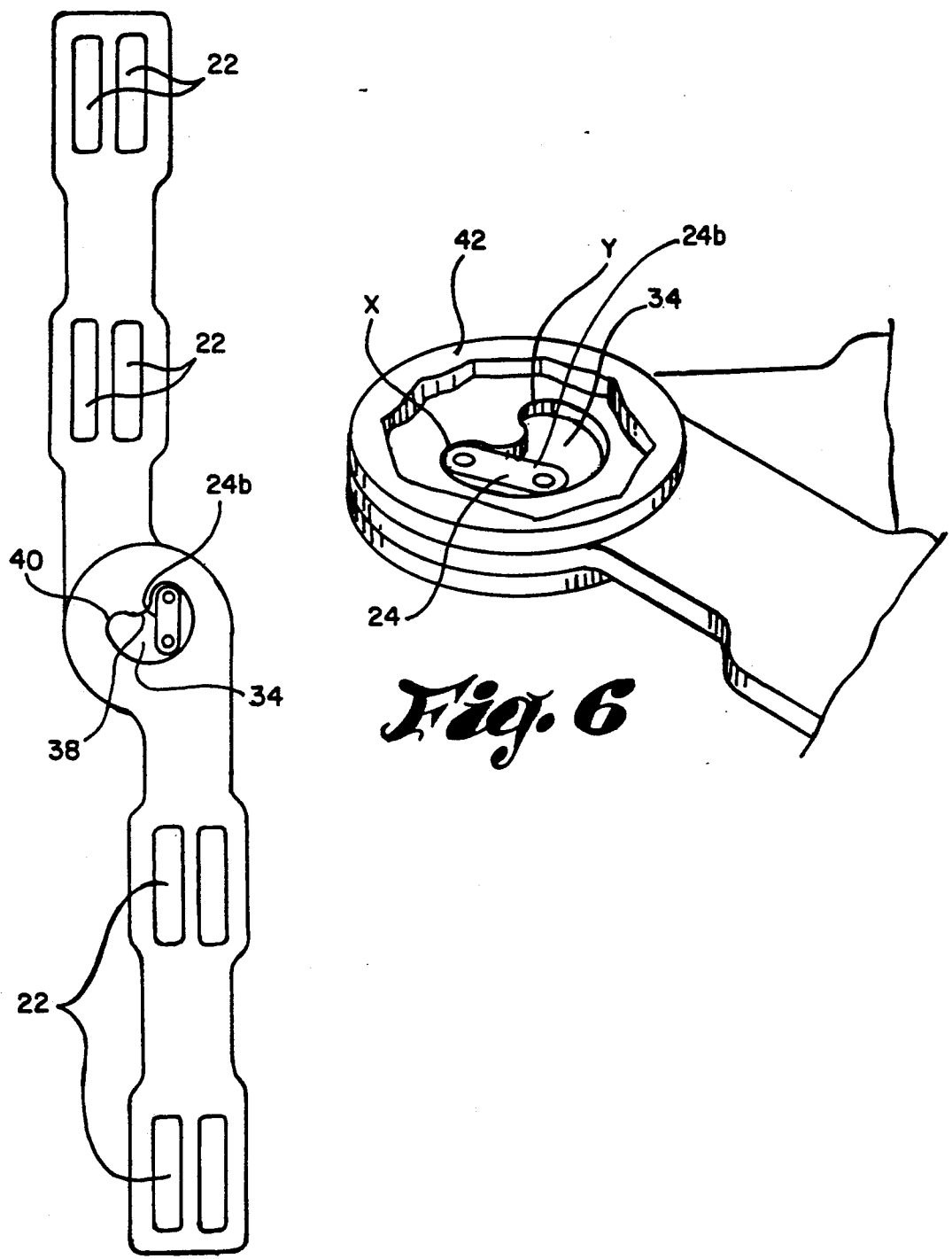

KNEE HINGE

BACKGROUND OF THE INVENTION

1. Field of the Invention

The present invention relates generally to orthopedic devices for controlling movement of human limbs, and more particularly to a hinge mechanism or mechanical joint for a knee brace which permits smooth articulation of the mechanical joint.

2. Description of Related Art

The human body seems prone to injury. Whether in use at work or at play, human joints, such as knee joints, elbow joints, and ankle joints, are particularly susceptible to impairment. Various devices and mechanisms have been developed to guard against injury and to assist in the healing process. The general aim of these devices is to replace some of the work performed by the human joint with work performed by the mechanical joint, thus assisting in the recuperative process.

Knee braces, in particular, are heavily used by professional and non-professional athletes to protect against knee injuries, to protect an injured knee, and to assist in the knee injury healing process. Several different kinds of braces are currently in use. Typically these devices employ hinge mechanisms which include ball bearings or pin and slot configurations. A common disadvantage to most earlier devices is that they have a tendency to lock up, stick, or catch during articulation of the joint. Another disadvantage is that earlier devices typically include multiple moving parts, thereby complicating the manufacturing and production process.

Applicants are aware of U.S. Pat. No. 4,890,607, entitled MULTIAXIS CONTROLLED MOTION KNEE ORTHOSIS, which issued to Townsend on Jan. 2, 1990, and which relates generally to a knee brace.

Townsend relates to orthopedic devices for the stabilization and control of a human knee joint which has been injured. The Townsend device relates to a multiaxis controlled motion knee orthosis in the form of a knee brace appliance wherein a joint mechanism is provided that utilizes two camming slots and cam pin followers to attempt an arthrokinematic movement comprised of an anterior motion of a femoral link relative to a tibial link during an initial phase of flexion followed by a unicentric phase of movement.

SUMMARY OF THE INVENTION

A knee brace is disclosed which includes a novel knee hinge having a first arm member, a second arm member, and a cover piece. The first arm member serves as a femoral brace. A cam follower is mounted on one side of the first arm member. The second arm member serves as a tibial brace. The second arm member includes a generally heart-shaped aperture which is a cam for the hinge. The cam defines a continuous cam wall which is adapted to receive and mate with the cam follower. The dimensions of the cam are such that upon engagement of the cam follower with the cam, each semicircular end of the cam follower is in slidable contact with the cam wall during movement of the cam follower, and the edge of the cam follower closest to the cam node is in slidable contact with the cam node during movement of the cam follower. The cam follower rotates about the cam node and permits a degree of motion between full flexion and full extension. The cover piece is a round, disc-shaped member adapted for placement atop the mated first and second arm members. The cover piece, second arm member, and first arm member, and cam follower are secured together by rivets. The cam follower is therefore bounded on its top by the cover piece, on its bottom by the first arm member, and on its sides by the cam wall of the second arm member.

OBJECTS OF THE INVENTION

The principal object of the invention is to provide a hinge mechanism or mechanical joint for a knee brace which permits smooth articulation of the mechanical joint.

A further object of the invention is to provide a hinge mechanism which does not stick or catch during articulation movement.

A further object of the invention is to provide a hinge mechanism with few moving parts.

Another object of the invention is to provide a hinge mechanism which is easy to manufacture and produce.

BRIEF DESCRIPTION OF THE DRAWINGS

The foregoing and other objects will become more readily apparent by referring to the following detailed description and the appended drawings, in which:

FIG. 1 is an isometric view of the invented knee hinge in use on a knee brace.

FIG. 2 is a partially exposed plan view of the invented knee hinge illustrating the cam and cam follower mechanism, with the hinge in a flexed position.

FIG. 2a is a sectional view of the first arm member with the cam follower mounted thereon.

FIG. 3 is a side view of the invented knee hinge, showing the cover piece secured to the cam follower and first arm member.

FIG. 4 is a plan view of the first arm member, second arm member, and cover piece, each shown in isolation.

FIG. 5 is a partially exposed plan view of the invented knee hinge illustrating the cam and cam follower mechanism, with the hinge in an extended position.

FIG. 6 is an elarged view of the cam and cam follower mechanism shown in FIG. 2.

DETAILED DESCRIPTION

Referring now to the drawings, and particularly to FIG. 1, a knee brace 10 incorporates the invented knee hinge 12. The knee hinge 12 includes a first arm member 14, a second arm member 26 rotatably engagable with the first arm member 14, and a cover piece 42 which retains the first and second arm members 14, 26. For purposes of the description, a single hinge 12 for a human knee is described. The invented hinge 12 may also be advantageously employed with respect to other limbs and in connection with other primates. Also, an entire knee brace 10 apparatus preferably includes two knee hinges 12a, 12b, one laterally positioned 12a relative to the knee joint, and one medially positioned 12b relative to the knee joint.

In the preferred embodiment, the first arm member 14 serves as a femoral brace. The first arm member 14 comprises a generally rigid paddle-like member advantageously shaped and adapted for placement in proximity with the upper portion of a human leg. The first arm member 14 is preferably made of an aluminum alloy, although other lightweight alloys may also be employed. The first arm member 14 also has one or more apertures 22 through which straps 52 or other binding means may pass. The straps 52 assist in securing the first arm member 14 to the upper portion of the leg. A support pad 54 may also be secured to the first arm member 14. FIG. 1 shows a support pad 54 secured to a first arm member with rivets 46.

As shown in FIG. 4, the first arm member 14 includes a head 16, a shank 18, and an end 20. The head 16 of the first arm member 14 is preferably rounded, having a diameter of approximately 1½ to 3 inches, and preferably about 2 inches. A boss or cam follower 24 is mounted on one side of the head 16. The cam follower 24 comprises an elongated bar-style member having semicircular ends 24a adapted for mating with cam lobes 40. The cam follower 24 measures approximately 1 inch in length, ⅜ inch in width, and has a depth of ⅛ inch. The dimensions of the cam follower 24 are such that upon engagement of the cam 34 with the cam follower 24, each semicircular end 24a of the cam follower 24 is in slidable contact with the cam wall 36 during movement of the cam follower 24, and the edge 24b of the cam follower 24 closest to the cam node 38 is in slidable contact with the cam node 38 during movement of the cam follower 24. The cam follower 24 is positioned on the first arm member head 16 so that the longitudinal axis of the cam follower 24 is generally parallel to the longitudinal axis of the shank 18. Although the cam follower 24 may be an integral part of the first arm member 14, it is preferable if it is a separate piece which is mounted to the first arm member head 16 with holding means, such as rivets 48.

The second arm member 26 serves as a tibial brace. The second arm member 26 comprises a generally rigid paddle-like member shaped and adapted for placement in proximity with the lower portion of a human leg. The second arm member 26 is made of the same material as the first arm member 14. As with the first arm member 14, the second arm member 26 has one or more apertures 22 through which straps 52 or other binding means may pass. The straps 52 assist in securing the second arm member 26 to the lower portion of the leg. A support pad 54 may also be secured to the second arm member 26. FIG. 1 shows a support pad 54 secured to the second arm member 26 with rivets 46.

The second arm member 26 includes a head 28, a shank 30, and an end 32. The head 28 of the second arm member 26 is preferably rounded, having a diameter of approximately 2 inches. The second arm member head 28 includes a heart-shaped aperture which is a cam 34 for the hinge 12. The cam 34 defines a continuous cam wall 36. The inwardly pointing portion of the heart shaped cam 34 shown in FIG. 4 is referred to herein as the cam node 38. The two sections of the heart shaped cam 34 formed by the cam node 38 are referred to herein as the cam lobes 40.

The cam 34 is adapted to receive and mate with the cam follower 24. The dimensions of the cam 34 are such that upon engagement of the cam follower 24 with the cam 34, each semicircular end 24a of the cam follower 24 is in slidable contact with the cam wall 36 during movement of the cam follower 24, and the edge 24b of the cam follower 24 closest to the cam node 38 is in slidable contact with the cam node 38 during movement of the cam follower 24. Thus, the cam 34 defines the path which the cam follower 24 must follow. The cam node 38 imposes a path of rotational motion on the first and second arm members 14, 26 coinciding with a path of motion exhibited by flexion and extension of a human knee. Each cam lobe 40 is adapted to receive an end 24a of the cam follower 24. The cam lobes 40 define stop points X, Y. Stop point X is the flexion stop point. Stop point Y is the extension stop point. FIG. 2 illustrates the hinge 12 as it would appear upon full flexion of the knee. FIG. 5 illustrates the hinge 12 as it would appear upon full extension of the knee. The cam follower 24 rotates about the cam node 38 and permits a degree of motion between full flexion and full extension, as defined by the cam lobes 40. Slidable contact between the cam follower 24 and the cam wall 36 permits smooth articulation of the mechanical joint.

The cover piece 42 is adapted for placement atop the mated first and second arm members 14, 26, and may be round, oval, or some other convenient shape. The cover piece 42 has at least one aperture 44 thereon for receiving holding means. A single aperture 44 may be used, but two apertures 44 are preferred. The cover piece apertures 44 are positioned so that upon placement of the cover piece 42 atop the first and second arm members 14, 26, the apertures 44 are aligned over the cam follower 24. The cover piece 42, second arm member 26, and first arm member 14 are secured by suitable holding means such as rivets 48, pins, or screws, which are inserted through rivet holes 49. FIG. 3 shows the preferred approach of using rivets 48 to secure the cover piece 42 and first and second arm members 14, 26. The cam follower 24 is therefore bounded on its top by the cover piece 42, on its bottom by the first arm member 14, and on its sides by the cam wall 36 of the second arm member 26.

SUMMARY OF THE ACHIEVEMENT OF THE OBJECTS OF THE INVENTION

From the foregoing, it is readily apparent that we have invented an improved hinge mechanism or mechanical joint for a knee brace which permits smooth articulation of the mechanical joint, which does not stick or catch during articulation movement, having few moving parts, which is easy to manufacture and produce.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

We claim:

1. A hinge for a limb brace which permits a range of motion for a limb between full extension and full flexion, comprising:
    (a) a first arm member adapted for attachment to a human limb;
    (b) an elongated boss having rounded ends positioned at one end of said first arm member;
    (c) a second arm member having a head end and an attachment end adapted for attachment to a human limb;
    (d) means for receiving a single boss, said boss-receiving means being integral with the head end of said second arm member on only one side thereof, where only said elongated boss and said boss-receiving means define a range of motion for said limb brace corresponding to a range of motion for a limb between full extension and full flexion;
    (e) said boss-receiving means comprising a generally round cam having an inwardly projecting rounded node creating a camming surface, wherein said boss is sized to have both rounded ends in continuous contact with the camming surface of said boss-receiving means throughout said range of motion; and (f) retaining means for securing said first arm member to said second arm member, while permitting movement of said boss within said receiving means, said first arm member and said second arm member being movable relative to one another in proportion to the range of motion of said boss within said boss receiving means.

2. The hinge according to claim 1, wherein said cam has a generally circular shape and defines a continuous cam wall, said cam node defining two cam lobes adapted for engaging said boss and allowing ample room for said boss to change its axis of rotation.

3. The hinge according to claim 2, wherein said cam imposes a path of rotational motion on said first and second arm members coinciding with a path of motion exhibited by flexion and extension of a human knee.

4. The hinge according to claim 1, wherein said first arm member and said second arm member are aligned so that said boss engages said boss-receiving mean, and said retaining means for securing said first arm member to said second arm member includes:

(a) a round, disc-shaped member adapted for placement atop said aligned first and second arm members, said disc-shaped member having at least one aperture therein, each aperture being positioned so that upon placement of the disc-shaped member atop said first and second arm members, each aperture is aligned over said boss;

(b) means inserted through each aperture and engaging said boss for holding said first arm member, said second arm member, and said disc-shaped member together; and (c) said round disc-shaped member fully covers said boss-receiving means, thereby inhibiting entry of foreign elements that could impede smooth movement of said boss about said cam.

5. The hinge according to claim 4, wherein said holding means is selected from the group consisting of rivets, pins, screws, and tack welds.

6. The hinge according to claim 1, wherein said limb brace is a knee brace.

7. The hinge according to claim 1, wherein said first member comprises a generally rigid member advantageously shaped and adapted for placement in proximity with the upper portion of a human limb.

8. The hinge according to claim 1, wherein said first member is made of a material selected from the group consisting of metals, alloys and plastics.

9. The hinge according to claim 1, further comprising said first member being provided with at least one aperture therethrough adapted for receiving binding means, and binding means received in said aperture.

10. The hinge according to claim 9, wherein said binding means is a strap.

11. The hinge according to claim 1, further comprising means for securing a support pad to said first arm member.

12. The hinge according to claim 1, wherein said first member includes a head, a shank, and an end, said head being rounded.

13. The hinge according to claim 12, wherein the head of said first member has a diameter of approximately 1½ to 3 inches.

14. The hinge according to claim 1, wherein said boss comprises a cam follower, said cam follower being an elongated bar-style member having a longitudinal axis and a first and second semicircular end, each end adapted for slidably rotating within said receiving means.

15. The hinge according to claim 14, wherein said cam follower engages said receiving means with each semicircular end of said cam follower in slidable contact with said receiving means during rotational movement.

16. The hinge according to claim 14, said first arm member having a head, a shank and an end, wherein said cam follower is positioned on said first arm member head with the longitudinal axis of said cam follower generally parallel to the longitudinal axis of said shank.

17. The hinge according to claim 14, wherein said cam follower is a separate piece from said first arm member, further comprising means for securing said cam follower to said first arm member.

18. The hinge according to claim 14, wherein said cam follower is integral with and upstanding from said first arm member.

19. The hinge according to claim 1, wherein said second member comprises a generally rigid member shaped and adapted for placement in proximity with the lower portion of a human limb.

20. The hinge according to claim 1, wherein said second member is made of a material selected from the group consisting of alloys and plastics.

21. The hinge according to claim 1, further comprising said second member having at least one aperture through which binding means may pass.

22. The hinge according to claim 1, further comprising means for securing a support pad to said second arm member.

23. The hinge according to claim 1, wherein said second member includes a head, a shank, and an end, said head being rounded and having a diameter of approximately 2 inches.

24. The hinge according to claim 1, wherein said cam defines a heart-shaped aperture.

* * * * *